United States Patent
Xu et al.

(10) Patent No.: US 10,329,711 B2
(45) Date of Patent: Jun. 25, 2019

(54) NONWOVEN WEB WITH IMPROVED CUT EDGE QUALITY, AND PROCESS FOR IMPARTING

(71) Applicant: The Procter & Gamble Company, Cincinnati, OH (US)

(72) Inventors: Han Xu, Cincinnati, OH (US); Andrew Starr Bales, Terrace Park, OH (US); Peter Wiedmann, Montgomery, OH (US); Taner Dirama, Istanbul (TR); Carlisle Mitchell Herron, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1234 days.

(21) Appl. No.: 14/316,859

(22) Filed: Jun. 27, 2014

(65) Prior Publication Data
US 2015/0004367 A1    Jan. 1, 2015

Related U.S. Application Data

(60) Provisional application No. 61/840,690, filed on Jun. 28, 2013.

(51) Int. Cl.
| | | |
|---|---|---|
| *D06H 7/00* | (2006.01) | |
| *A61F 13/00* | (2006.01) | |
| *D04H 1/00* | (2006.01) | |
| *B32B 38/00* | (2006.01) | |
| *B32B 37/00* | (2006.01) | |

(Continued)

(52) U.S. Cl.
CPC ....... *D06H 7/005* (2013.01); *A61F 13/15723* (2013.01); *A61F 13/15739* (2013.01); *D04H 1/541* (2013.01); *D04H 1/542* (2013.01); *B32B 37/24* (2013.01); *Y10T 156/1023* (2015.01); *Y10T 156/1039* (2015.01); *Y10T 156/1043* (2015.01); *Y10T 428/24603* (2015.01)

(58) Field of Classification Search
None
See application file for complete search history.

(56) References Cited

U.S. PATENT DOCUMENTS

| | | |
|---|---|---|
| 2,952,260 A | 9/1960 | Burgeni |
| 4,016,628 A | 4/1977 | Kolbach |

(Continued)

OTHER PUBLICATIONS

PCT International Search Report, dated Oct. 17, 2014 (10 pages).

*Primary Examiner* — Linda L Gray
(74) *Attorney, Agent, or Firm* — William E. Gallagher; Charles R. Matson

(57) ABSTRACT

A process for producing a nonwoven web material with improved edge quality, and the product thereof, are disclosed. The process may include the steps of forming a batt of polymeric fibers; consolidating the batt in a z-direction and thereby forming a nonwoven web material, conveying the nonwoven web material to a nip between a bonding roller and anvil roller, and impressing a pattern of bond impressions into the nonwoven web material, the bond impressions lying along a cut path. When the web is subsequently cut along the cut path, fibers proximate the cut path are immobilized by the bonds, providing for relatively neater, cleaner cut edges and reducing the number of loose fibers that may be released into the plant environment in downstream processing operations.

7 Claims, 8 Drawing Sheets

(51) Int. Cl.
*A61F 13/15* (2006.01)
*D04H 1/541* (2012.01)
*D04H 1/542* (2012.01)
B32B 37/24 (2006.01)

(56) References Cited

U.S. PATENT DOCUMENTS

| | | | |
|---|---|---|---|
| 4,590,114 A * | 5/1986 | Holtman | A61L 15/24 |
| | | | 156/209 |
| 4,994,053 A | 2/1991 | Lang | |
| 5,266,392 A | 11/1993 | Land et al. | |
| 5,370,764 A | 12/1994 | Alikhan | |
| 6,203,654 B1 | 3/2001 | McFall et al. | |
| 6,321,425 B1 | 11/2001 | Putnam et al. | |
| 6,430,788 B1 | 8/2002 | Putnam et al. | |
| 6,551,436 B1 | 4/2003 | Flohr et al. | |
| 6,863,933 B2 | 3/2005 | Cramer et al. | |
| 6,905,987 B2 * | 6/2005 | Noda | B32B 27/20 |
| | | | 442/364 |
| 6,921,570 B2 | 7/2005 | Belau et al. | |
| 7,112,621 B2 | 9/2006 | Rohrbaugh et al. | |
| 7,276,642 B2 | 10/2007 | Belau | |
| 7,858,544 B2 | 12/2010 | Turi et al. | |
| 8,093,163 B2 | 1/2012 | Turi et al. | |
| 8,728,051 B2 | 5/2014 | Lu et al. | |
| 2002/0168910 A1 | 11/2002 | Vuillaume et al. | |
| 2003/0148684 A1 | 8/2003 | Cramer et al. | |
| 2004/0010894 A1 | 1/2004 | Goldwasser et al. | |
| 2004/0094004 A1 | 5/2004 | Julius | |
| 2005/0008839 A1 | 1/2005 | Cramer et al. | |
| 2007/0044903 A1 | 3/2007 | Wineski et al. | |
| 2012/0152446 A1 | 6/2012 | Rhodes et al. | |
| 2012/0286647 A1 | 11/2012 | Schmidt et al. | |

* cited by examiner

NONWOVEN WEB WITH IMPROVED CUT EDGE QUALITY, AND PROCESS FOR IMPARTING

BACKGROUND OF THE INVENTION

Many products include components formed from nonwoven webs of polymeric fibers. Products such as filtration media, disposable surgical garments, disposable cleaning cloths, disposable personal cleansing wipes and towels, bandages and wound dressings, disposable diapers and training pants, adult incontinence pants and feminine hygiene pads are only a few examples.

Consumer products such as disposable diapers may include a number of components formed of nonwoven web materials, such as backsheet outer layers, topsheets, and barrier cuffs. The nonwoven web supply material is typically formed in a relatively wide, continuous sheet, which is then cut or slit to suitable cross direction widths and machine direction lengths to form components during the process of manufacturing such products. A typical disposable diaper may have a number of exposed cut edges of nonwoven web about its perimeter and/or other locations. Nonwoven web components other types of products may also have exposed cut edges.

The cut edges of such components are often formed in a relatively high speed process in which a nonwoven web is conveyed in the machine direction, through the nip of a cutting mechanism. The cutting mechanism may comprise a pair of offset circular blades with overlapping perimeter cutting edges that are formed and disposed to meet in shearing/scissors fashion, while rotating on axes above and below the web and approximately parallel with the cross direction, thereby continuously scissoring the web along the machine direction. In an alternative cutting mechanism, a rotating cutting blade having a perimeter cutting edge may be disposed to meet an opposing rotating anvil roller having a smooth surface, to form a cutting nip. Regardless which process may be used, there are shortcomings.

First, particularly when a cutting blade is less than fully sharp as after some use, as it encounters fibers in the web as the web is conveyed into the shearing/cutting nip, the dulled cutting edge may tend to displace the fibers within the web before severing them, in a manner similar to what occurs when one tries to cut a fibrous web with a dull scissors. As a result, the cut edge may have a ragged form and appearance rather than a neat, clean cut form and appearance. This can present complications in downstream processing. Further, if a product has nonwoven components with such ragged edges exposed, consumers may have negative perceptions of the quality of the product.

Second, in many types of nonwoven webs the individual fibers thereof may only be loosely bound within the web. Particularly in (but not unique to) webs formed of low bond area percentage or shorter fibers or staple fibers, cutting the web and further downstream operations may cause individual fibers that are randomly cut short near the edge in the shearing/cutting operation, and are not securely bound within the web, to work loose and be released into the plant environment. This may contribute to imparting to the cut edge an undesirable frayed structure and appearance, and, depending upon the severity of the situation, can create significant industrial hygiene problems. Loose fibers, often airborne, can accumulate and cause problems with plant environment equipment and processes. It is often necessary to install and operate costly vacuum systems to collect such fibers, and even these are not completely successful. Additionally, periodic shutdown of lines for removal of substantial accumulations of loose fibers is often necessary.

Regardless of whether the cutting blade used to cut the web is sharp and the web is formed of long fibers, fibers along cut edges may be displaced or dislodged in downstream operations, resulting in a frayed and/or uneven edge.

For these reasons, there is a need for improvement in the nonwoven web cutting, slitting and/or shearing process and the resulting product.

DESCRIPTION OF THE FIGURES

Like features are given like numbers throughout the figures.

DESCRIPTION OF EXAMPLES OF EMBODIMENTS

Definitions

Figure 1:
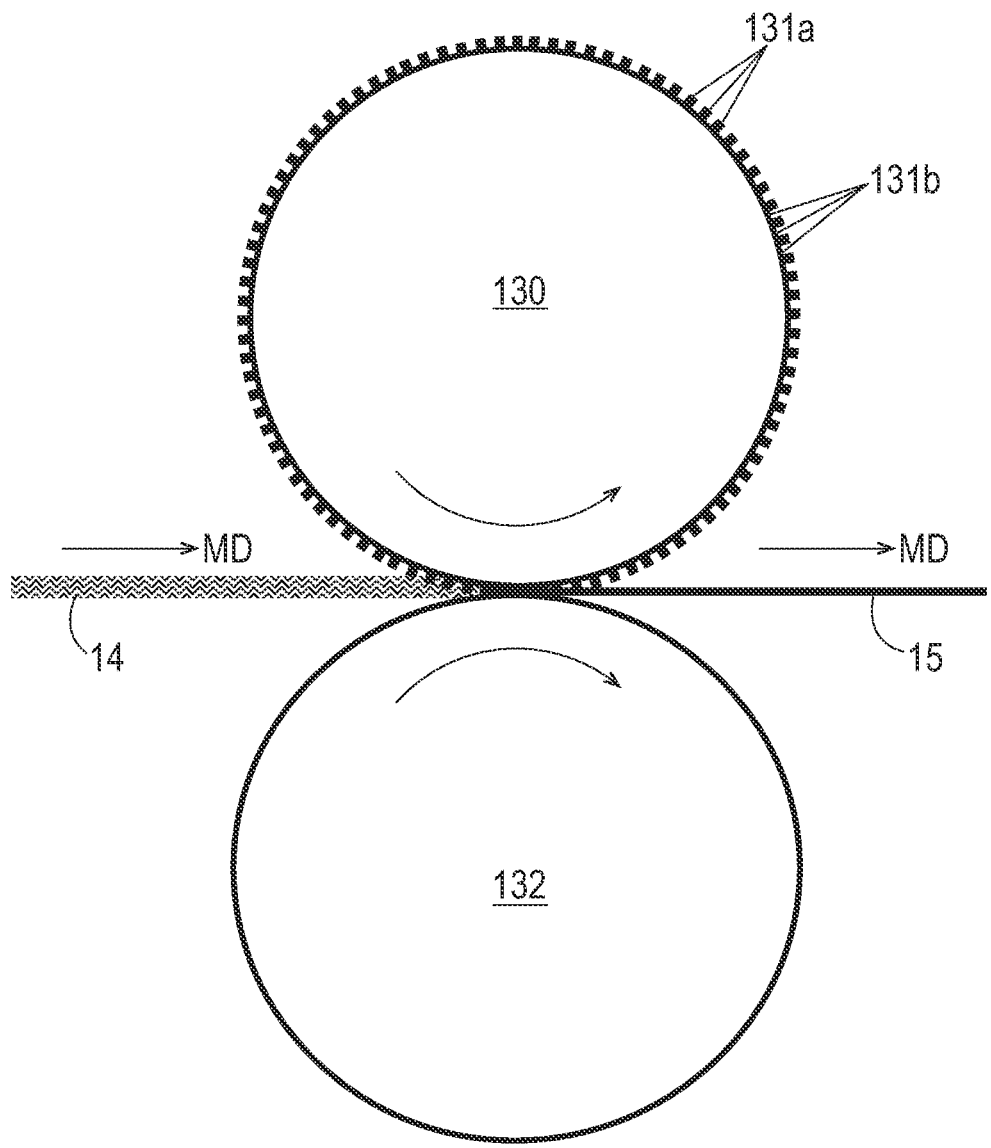
FIG. 1 is a schematic side view of a pair of calendar rollers converting a nonwoven batt into a nonwoven web, viewed along the cross direction.
Figure 2:
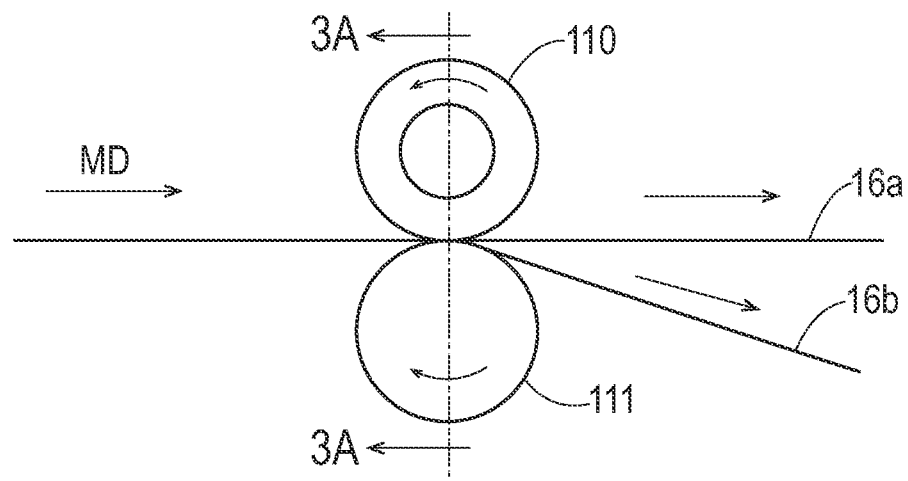
FIG. 2 is a schematic side view of a pair of rotating shearing blades cutting a nonwoven web along the machine direction, viewed along the cross direction.

A "batt" is used herein to refer to an accumulation of fibers produced and laid down in a spinning process or other nonwoven web manufacturing process, prior to being consolidated in a calendering and bonding process as described herein. A "batt" comprises individual fibers, which are usually unbonded to each other, although a certain amount of pre-bonding between fibers may be performed and is also included in the meaning, such as may occur during or shortly after the lay-down of fibers in a spunlaying process, or as may be achieved by pre-calendering. This pre-bonding, however, still permits a substantial number of the fibers to be freely moveable such that they can be repositioned. A "batt" may comprise several strata, such as may result from depositing fibers from several beams or banks of spinnerets in a spunlaying process.

"Bicomponent" refers to fiber having a cross-section comprising two discrete polymer components, two discrete blends of polymer components, or one discrete polymer component and one discrete blend of polymer components. "Bicomponent fiber" is encompassed within the term "multicomponent fiber." A bicomponent fiber may have an overall cross section divided into two or more subsections of the differing components of any shape or arrangement, including, for example, coaxial subsections, core-and-sheath subsections, side-by-side subsections, radial subsections, etc.

"Bond area percentage" on a nonwoven web is a ratio of area occupied by bond impressions, per unit surface area of the web on the side in which the impressions are impressed, expressed as a percentage, and measured according to the Bond Area Percentage Method set forth herein.

"Bonding roller," "calender roller" and "roller" are used interchangeably.

A "bond impression" in a nonwoven web is the surface structure created by the impression of a bonding protrusion on a calender roller into a nonwoven web. A bond impression is a location of compressed, deformed, intermeshed or entangled, and/or thermally fused, fibers superimposed and compressed in a z-direction beneath the bonding protrusion, which firm a bond. The individual bonds may be connected in the nonwoven structure by loose fibers between them. The shape and size of the bond impression approximately corresponds to the shape and size of the bonding surface of a bonding protrusion on the calender roller.

Bond impression "density," with respect to a pattern of bond impressions impressed into a nonwoven web material, relates to the number of discrete bond impressions per unit surface area of the web material.

A "bonding protrusion" or "protrusion" is a feature of a bonding roller at its radially outermost portion, defined by recessed areas. Relative the rotational axis of the bonding roller, a bonding protrusion has a radially outermost bonding surface with a bonding surface shape and a bonding surface shape area, which generally lies along and defines an outer cylindrical surface with a substantially constant radius from the bonding roller rotational axis; however, protrusions having bonding surfaces of discrete and separate shapes are often small enough relative the radius of the bonding roller that the bonding surface may appear flat/planar; and the bonding surface shape area is closely approximated by a planar area of the same shape. A bonding protrusion may have sides that are perpendicular to the bonding surface, although usually the sides have an angled slope, such that the cross section of the base of a bonding protrusion at recessed areas is larger than its bonding surface. A plurality of bonding protrusions may be arranged on a calender roller in a pattern. The plurality of bonding protrusions has a bonding area per unit surface area of the outer cylindrical surface in which the bonding shapes lie, at the portion of the roller which will roll over the nonwoven material to be bonded, which can be expressed as a percentage, and is the ratio of the combined total of the bonding shape areas of the protrusions within the portion, to the total surface area of the portion ("bonding area percentage").

Bonding protrusion "density," with respect to a pattern of discrete bonding protrusions formed on a bonding roller, refers to the number of discrete bonding protrusions per unit cylindrical surface area of the roller.

"Cross direction" (CD)—with respect to the making of a nonwoven web material and the nonwoven web material, refers to the direction along the web material substantially perpendicular to the direction of forward travel of the web material through the manufacturing line in which the web material is manufactured. With respect to a batt moving through the nip of a pair of calender rollers to form a bonded nonwoven web, the cross direction is perpendicular to the direction of movement through the nip, and parallel to the nip.

"Film"—means a skin-like or membrane-like layer of material formed of one or more polymers, which does not have a form consisting predominately of a web-like structure of consolidated polymer fibers and/or other fibers.

"Machine direction" (MD)—with respect to the making of a nonwoven web material and the nonwoven web material, refers to the direction along the web material substantially parallel to the direction of forward travel of the web material through the manufacturing line in which the web material is manufactured. With respect to a nonwoven batt moving through the nip of a pair of calender rollers to form a bonded nonwoven web, the machine direction is parallel to the direction of movement through the nip, and perpendicular to the nip.

"Monocomponent" refers to fiber formed of a single polymer component or single blend of polymer components, as distinguished from bicomponent or multicomponent fiber.

"Multicomponent" refers to fiber having a cross-section comprising more than one discrete polymer component, more than one discrete blend of polymer components, or at least one discrete polymer component and at least one discrete blend of polymer components. "Multicomponent fiber" includes, but is not limited to, "bicomponent fiber." A multicomponent fiber may have an overall cross section divided into subsections of the differing components of any shape or arrangement, including, for example, coaxial subsections, core-and-sheath subsections, side-by-side subsections, radial subsections, islands-in-the-sea, etc.

A "nonwoven" is a manufactured sheet or web of directionally or randomly oriented fibers which are first formed into a batt and then consolidated and bonded together by friction, cohesion, adhesion or one or more patterns of bonds and bond impressions created through localized compression and/or application of pressure, heat, ultrasonic or heating energy, or a combination thereof. The term does not include fabrics which are woven, knitted, or stitch-bonded with yarns or filaments. The fibers may be of natural or man-made origin and may be staple or continuous filaments or be formed in situ. Commercially available fibers have diameters ranging from less than about 0.001 mm to more than about 0.2 mm and they come in several different forms: short fibers (known as staple, or chopped), continuous single fibers (filaments or monofilaments), untwisted bundles of continuous filaments (tow), and twisted bundles of continuous filaments (yarn). Nonwoven fabrics can be formed by many processes including but not limited to meltblowing, spunbonding, spunmelting, solvent spinning, electrospinning, carding, film fibrillation, melt-film fibrillation, airlaying, dry-laying, wetlaying with staple fibers, and combinations of these processes as known in the art. The basis weight of nonwoven fabrics is usually expressed in grams per square meter (gsm). Herein, a "nonwoven" or "nonwoven web" is distinguished from a "film" (also defined herein).

"Z-direction," with respect to a web, means the direction orthogonal to the machine and cross directions, or alternatively, for a web laid out flat and approximately defining a plane, the direction orthogonal to the plane.

Description

Nonwoven web materials to which the present invention may be applied include, but are not limited to spunbond, meltblown, spunmelt, solvent-spun, electrospun, carded, film fibrillated, melt-film fibrillated, air-laid, dry-laid, wet-laid staple fibers, and other and other nonwoven web materials formed in part or in whole of polymer fibers, as known in the art. A suitable nonwoven web material may also be an SMS material, comprising a spunbonded, a melt-blown and a further spunbonded stratum or layer or any other combination of spunbonded and melt-blown layers, such as a SMMS or SSMMS etc. Examples include one or more layers of fibers with diameters below 1 micron (nanofibers and nanofiber layers); examples of these rise in combinations of SNS, SMNS, SSMNS or SMNMS nonwoven webs (where "N" designates a nanofiber layer). In some examples, permanently hydrophilic non-wovens, and in particular, non-wovens with durably hydrophilic coatings may be desirable. Typically, the suitable nonwoven is air permeable. Typically the suitable nonwoven is water or liquid permeable, but may also be water impermeable by reason of fiber size and density, and hydrophobicity of the fibers. Water or liquid permeability may be enhanced by treatments to render the fibers hydrophilic.

The nonwoven web may be formed predominately of polymeric fibers. The fibers may be formed from one or more resins of polyolefins, polyesters or polyamides, including but not limited to polypropylene (PP), polyethylene (PE), and polyethylene terephthalate (PET), polyamides (e.g., Nylon) poly-lactic acid (PLA), and blends thereof. Resins including polypropylene may be particularly useful because of polypropylene's relatively low cost and surface friction properties of fibers formed from it (i.e., they have a relatively smooth, slippery tactile feel). Resins including polyethylene may also be desirable because of polyethylene's relative softness/pliability and even more smooth/slippery surface friction properties. Relative each other, PP currently has a lower cost and fibers formed from it have a greater tensile strength, while PE currently has a greater cost and fibers formed from it have a lower tensile strength but greater pliability and a more smooth/slippery feel. Accordingly, it may be desirable to form nonwoven web fibers from a blend of PP and PE resins, finding a balance of the best proportions of the polymers to balance their advantages and disadvantages. In some examples, the fibers may be formed of PP/PE blends such as described in U.S. Pat. No. 5,266,392. Nonwoven fibers may be formed of, or may include as additives or modifiers, components such as aliphatic polyesters, thermoplastic polysaccharides, or other biopolymers.

The individual fibers may be monocomponent or multicomponent. The multicomponent fibers may be bicomponent, such as in a core-and-sheath or side-by-side arrangement. Often, the individual components comprise aliphatic polyolefins such as polypropylene or polyethylene, or their copolymers, aliphatic polyesters, thermoplastic polysaccharides or other biopolymers.

Further useful nonwovens, fiber compositions, formations of fibers and nonwovens and related methods are described in U.S. Pat. No. 6,645,569 to Cramer et al., U.S. Pat. No. 6,863,933 to Cramer et al., U.S. Pat. No. 7,112,621 to Rohrbaugh et al.; co-pending U.S. patent application Ser. Nos. 10/338,603 and 10/338,610 by Cramer et al., and Ser. No. 13/005,237 by Lu et al., the disclosures of which are incorporated by reference herein.

A batt of fibers may be formed from any of these resins by conventional methods, such as carding, meltblowing, spunlaying, airlaying, wet-laying etc. A preferred execution relates to spunbonding processes, in which the resin(s) are heated and forced under pressure through spinnerets. The spinnerets eject streams of the molten polymer(s), which are then cooled to form fibers and directed onto a moving belt; as they strike the moving belt they may be laid down in somewhat random orientations, but often with a machine-direction orientation or bias, to form a spunlaid batt. The batt then may be calender bonded to form the nonwoven web.

Nonwovens of any basis weight are contemplated. However, relatively higher basis weight, while having relatively greater apparent caliper and loft, also has relatively greater cost. In examples in which a nonwoven web will form a component of a diaper such as a diaper backsheet nonwoven or topsheet, a nonwoven having a basis weight from 6.0 to 50 gsm, more preferably from 8.0 to 35 gsm, even more preferably from 9.0 to 25 gsm, and still more preferably from 10 to 20 gsm are contemplated. In some applications that may be applicable to use of the material to form disposable diaper topsheets or backsheet outer covers, a nonwoven having a basis weight from 3.0 to 25 gsm may be considered. When used as a component of an absorbent article such as a topsheet, a lower basis weight nonwoven may provide strikethrough superior to that of a higher basis weight nonwoven. In other applications, such as, for example, use of nonwovens to form products such as disposable clothing articles, wipes or dusters, higher basis weights up to 100 gsm, or even 150 gsm, may be desired. Optimal basis weight is dictated by the differing needs in each application, and cost concerns.

In one example, a spunbonding process of nonwoven web manufacturing includes the step of calender bonding a batt of spunlaid fibers, to consolidate the fibers and bond them together to some extent to create and maintain a relatively stable fabric-like structure, and enhance mechanical properties tensile strength, which may be desirable so the material can sufficiently maintain structural integrity and dimensional stability in subsequent manufacturing processes, and in the final product in use. Referring to FIG. 1, calender bonding may be accomplished by conveying the batt 14 into and through the nip between a pair of rotating calender rollers 130, 132, thereby compressing and consolidating the fibers in the z-direction to form a nonwoven web 15. One or both of the rollers may be heated, no as to promote heating, plastic deformation, intermeshing and thermal bonding or fusion between superimposed fibers compressed at the nip. The rollers may form operable components of a bonding mechanism in which they are urged together by a controllable amount of force, so as to exert the desired compressing force/pressure at the nip. In some processes energy sources that generate energy in the form of ultrasound vibration, radiofrequency radiation, and/or thermal energy may be included in the bonding mechanism so as to transmit to or generate heat energy within the fibers, again, to enhance bonding.

One or both of the rollers may have their circumferential surfaces machined, etched, engraved or otherwise formed to have thereon a pattern of bonding protrusions 131a and recessed areas 131b, so that bonding pressure exerted on the batt at the nip is concentrated at the radially outermost surfaces (bonding surfaces) of the bonding protrusions 131a, and is substantially reduced at the recessed areas. The bonding surfaces have bonding surface shapes. As a result, an impressed pattern of bonds between fibers forming the web, having bond impressions in a pattern and of shapes corresponding to the pattern and shapes and of the bonding surfaces of the bonding protrusions 131a on the roller, is formed on the nonwoven web. Within the bond impressions created on the web, superimposed fibers are compressed and deformed about one another, and may be partially or entirely fused together. One roller such as roller 132 may have a smooth, unpatterned cylindrical surface so as to constitute an anvil roller, and the other roller 130 may be formed with a pattern as described, to constitute a bonding pattern roller; this combination of rollers wilt impart a pattern on the web reflecting the pattern on the bonding pattern roller. In some examples both rollers may be formed with patterns, and in particular examples, differing patterns that work in combination to impress a combination pattern on the web such as described in, for example, U.S. Pat. No. 5,370,764.

Figure 6:
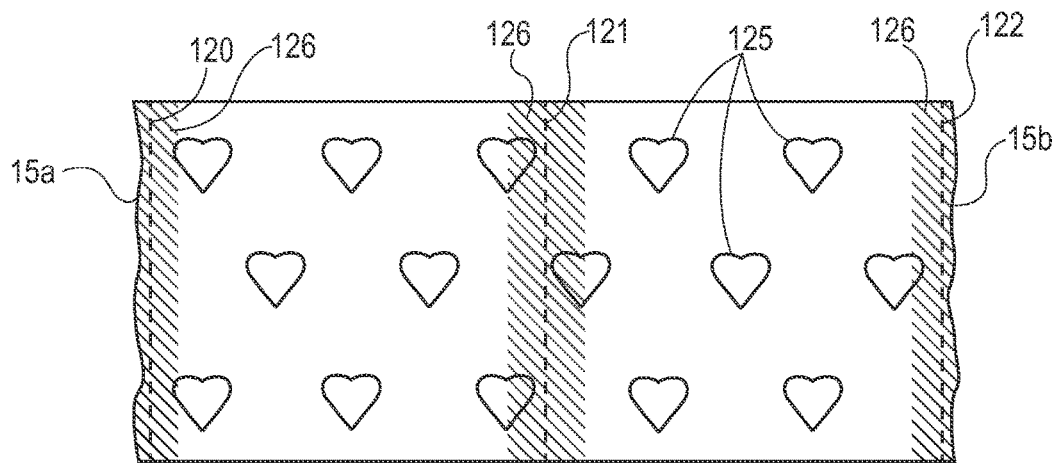
FIG. 6 is a schematic view of a portion of a nonwoven web, viewed along the z-direction.
Figure 7:
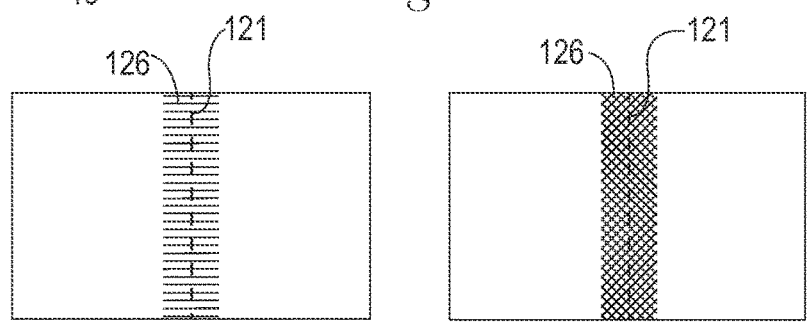
FIG. 7 is a schematic view of a portion of a nonwoven web, viewed along the z-direction.
Figure 8:
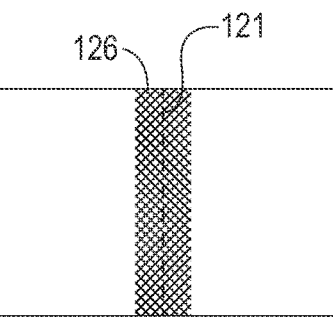
FIG. 8 is a schematic view of a portion of a nonwoven web, viewed along the z-direction.
Figure 9:
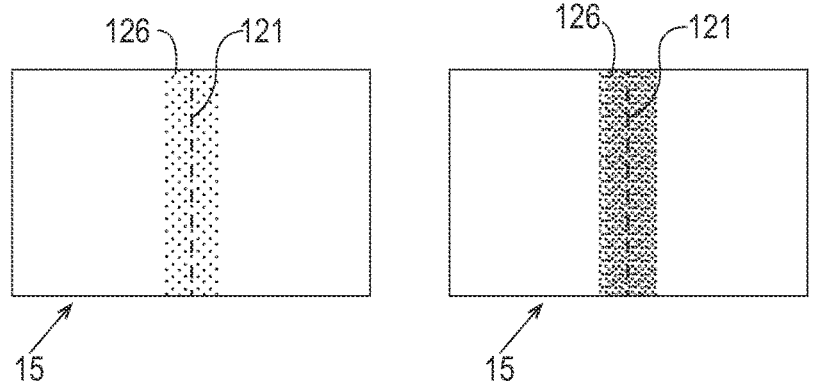
FIG. 9 is a schematic view of a portion of a nonwoven web, viewed along the z-direction.
Figure 10:
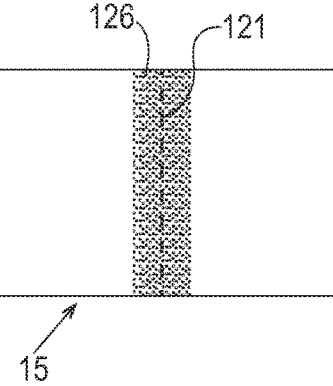
FIG. 10 is a schematic view of a portion of a nonwoven web, viewed along the z-direction.

A repeating pattern of bonding protrusions 131a and recessed areas 131b may be formed onto a bonding roller 130. Referring to FIG. 6, bond impressions 125 impressed into a nonwoven web may reflect the shapes of raised surfaces of bonding protrusions a on a roller 130 (e.g., FIG. 1), while the areas between and/or within the bond impressions 125 may reflect recessed areas 131b on the roller 130. The shapes of the bonding protrusions 131a impress like-shaped bond impressions on the web in the calender bonding process.

In another example, calender bonding need not involve use of bonding protrusions and creation of thermal bond sites. Rather, heat energy may be supplied by passing hot air through an unhanded web to melt at least a portion of the fibers to create bonding between fibers. In some examples both rollers 130, 132 may be smooth and may lightly compress the batt in the z-direction without concentrating pressure at bonding protrusions that form discrete bond impressions, thereby serving merely to somewhat consolidate the batt without bonding the fibers. In some examples where thermal or heat bonding is not desired, or in addition thereto, a resin, adhesive or other bonding agent may be introduced to the batt upstream or downstream of the nip between the rollers to effect bonding between the fibers within the web.

In still another example, loose friction bonding of the fibers to form a consolidated web may be effected by hydroentanglement, hydroengorgement or water needling processes such as described in, for example, U.S. Pat. Nos. 6,430,788; 6,321,425; 7,858,544 and 8,093,163, and U.S. Pat. App. Pub Nos. 2002/0168910 and 2004/0010894.

Figure 3A:
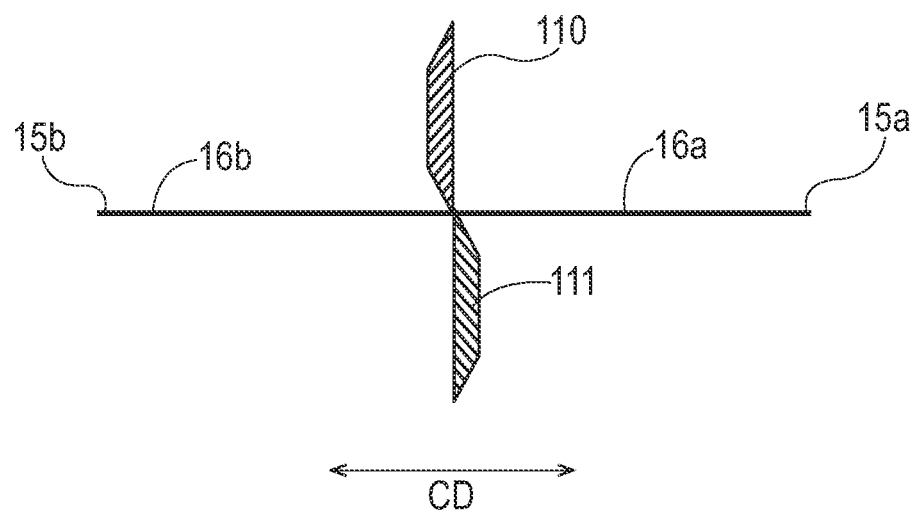
FIG. 3A is schematic cross-sectional view 3A-3A of the shearing blades as indicated in FIG. 2, viewed along the machine direction.
Figure 3B:
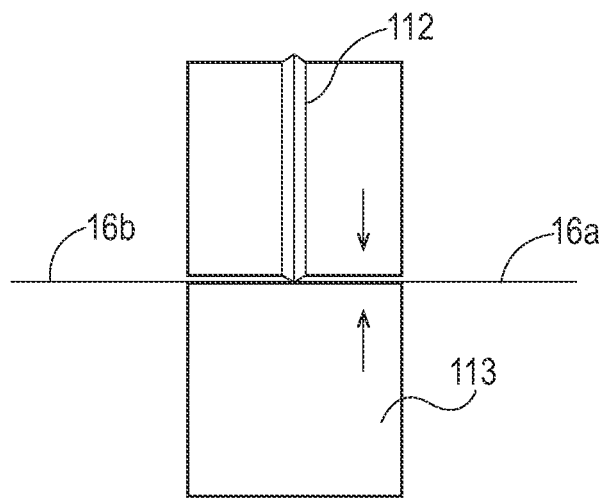
FIG. 3B is a schematic view of a cutting blade and an anvil roller cutting a nonwoven web along the machine direction, viewed along the machine direction.
Figure 3C:
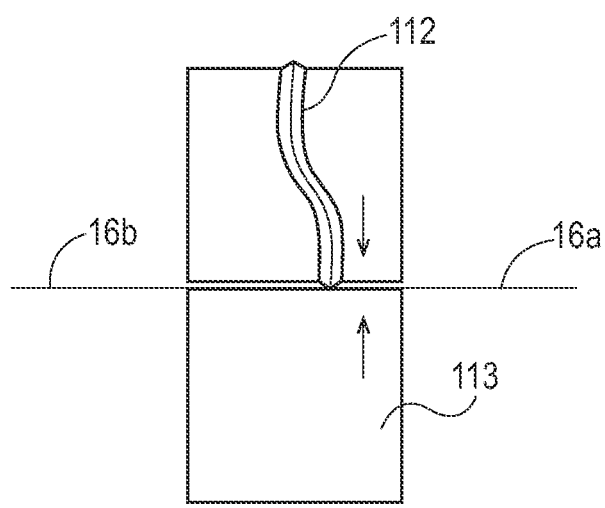
FIG. 3C is a schematic view of a cutting blade having a laterally varying cutting path and an anvil roller cutting a nonwoven web generally along the machine direction, viewed along the machine direction.

FIGS. 2 and 3A-3C schematically depict a machine-direction web cutting or slitting operation that might be employed in a process downstream of the calender bonding operation depicted in FIG. 1. Rotating shearing blades 110, 111 may be arranged in a web processing line to cut or slit a nonwoven web 15 being conveyed in a machine direction MD, along a cut path parallel with machine direction MD. The cutting or slitting operation cuts and separates the web into cut sections 16a, 16b. Referring to FIGS. 3B and 3C, it can be seen that, as an alternative, a single rotating cutting blade 112 meeting an anvil roller 113 at a cutting nip may serve the web cutting function, effecting cutting in nip fashion rather than shearing fashion. It will be further appreciated that nonwoven web 15 as manufactured prior to cutting may have an extended cross direction CD width, and a plurality of shearing blade or rotating cutting blade/anvil roller pairs may be disposed across the cross direction to cut the web into a plurality of cross-direction widths. Additionally, a typical nonwoven web prior to cutting has irregular side edges 15a, 15b (see, e.g., FIG. 6) as a result of the manner in which it is manufactured. It is common to cut off the irregular side edges in the manner described above, so as to impart straight side edges to the web.

Further, referring to FIG. 3C, a cutting mechanism may be configured with a rotating cutting blade 112 that follows a cutting path that varies in the cross direction, to effect a cut edge in the web that varies along the cross direction. Such a configuration may be desired in certain circumstances, for example, when a web is to be cut along a curved or other profile that varies along the cross direction.

Figure 4:
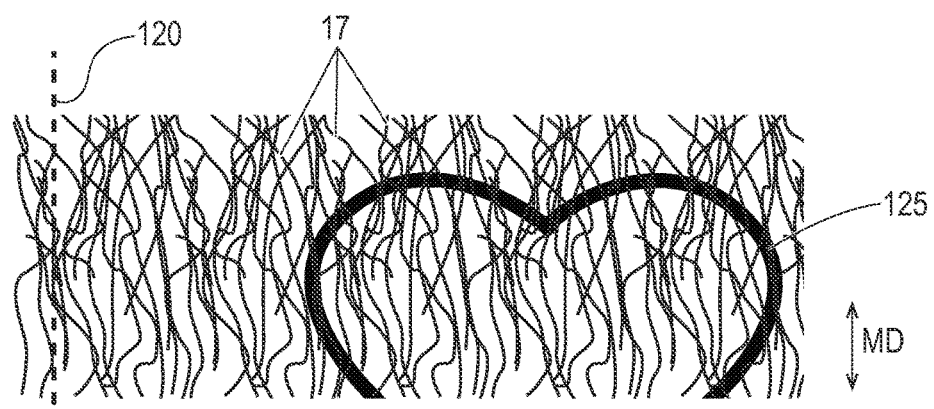
FIG. 4 is a schematic view of a portion of a nonwoven web, viewed along the z-direction.
Figure 5:
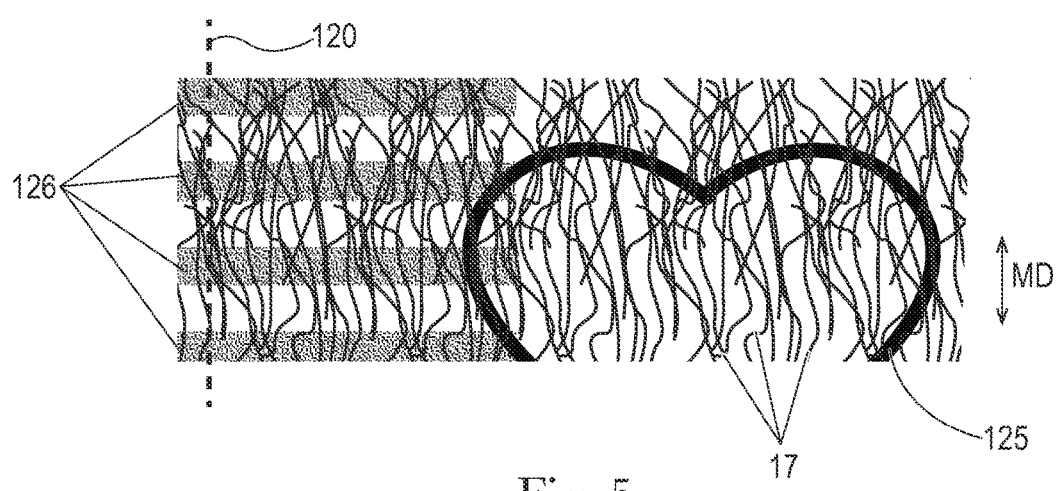
FIG. 5 is a schematic view of a portion of a nonwoven web, viewed along the z-direction.

FIG. 4 depicts an enlarged schematic view along the z-direction of a portion of a nonwoven web 15 composed of a multitude of fibers 17 and bearing bond impressions 125. In many nonwoven web manufacturing processes, individual fibers 17 are formed by ejecting molten polymer material through banks of spinnerets. Ejected polymer streams descend from the spinnerets, cooling to form fibers as they do so, and may be directed onto a horizontal belt having a substantial cross direction width and moving in the machine direction, onto which the fibers collect and accumulate to form a batt of fibers of varying lengths and orientations. The moving belt conveys the bat in the machine direction to the nip between a pair of calender rollers (e.g. FIG. 1), in which the bat 14 is compressed and consolidated in the z-direction to form a web. As noted above, the calendering process may include bonding in which bond impressions 125 are impressed into the web.

It can be appreciated that, when a web of such fibers is passed through the cutting nip between a pair of shearing blades or a cutting blade and anvil roller, along, e.g., cut path 120, individual fibers may be urged to displace within the web in front of the cutting nip particularly if the cutting blade is, or shearing blades are, relatively dull and do not sever the fibers quickly as they contact the blade(s). Even if the blade(s) are sharp, relatively loose fibers can be dis-placed or dislodged in downstream operations. As noted, this can result in an undesirably ragged or frayed cut edge. It will be further appreciated that when the web is cut along, e.g., cut path 120, some fibers may be severed from bonds to which they are connected, and thus, may no longer be bonded to the web; or they may be cut such that reduced and sometimes only relatively very short lengths of their remaining portions are present within the web along the cut edges, on either side of the cut. If the fibers in the web are not securely bound within the web (such as by being captured by a bond), these shortened lengths may easily dislodge and be released into the plant environment in downstream operations. This situation may result in frayed cut edges on the cut web portions; and the released fibers may be a source of plant and equipment contamination. It is believed that a large fraction of the unbound, loose/free small fiber fragments ("fiber dust") carried in a roll of nonwoven web is generated in cutting or slitting processes. The problem may be exacerbated when the nonwoven web is formed of staple-length fibers, which are relatively shorter than other types of fibers. The problem may also be exacerbated when the nonwoven web is formed bicomponent fibers or multi-component fibers, which may tend to be curly, more lofty, relatively more mobile relative the web structure, and have greater free lengths unbonded within the web structure.

A simple solution might be to simply increase the proportion of the surface area occupied by a pattern of bond impressions 125, thus increasing the proportion of fibers that will be captured by bonds along the cut edges. However, increasing bond area percentage in the nonwoven may compromise desired qualities of the nonwoven web product such as softness, drape and loft. A nonwoven bearing a relatively greater bond area percentage will usually be stiffer and less pliable, and will have less loft, than a nonwoven bearing a relatively lesser bond area percentage, all other variables being the same. Pliability and loft may be important attributes of softness.

Another solution might be to use laser rather than a mechanical cutting device, to cut the web and thermally bond fibers at the cut edges. This process, however, may require substantial investment in equipment, and may create cut edges that have a scratchy and uncomfortable feel.

Accordingly, it may be preferable that the main pattern of bond impressions have a bond area percentage from 5 to 45 percent, more preferably from 5 to 30 percent, and even more preferably from 10 to 20 percent. Alternatively, it may be preferable that the calender roller 130 bearing the main pattern of bonding protrusions, have a bonding area percentage of from 5 to 45 percent, more preferably from 5 to 30 percent, and even more preferably from 10 to 20 percent, combinations of these ranges, along the portion which rolls over the nonwoven during the bonding process. Bonding area percentage and/or bonding protrusion density are sometimes specified in engineering drawings and/or specifications for the manufacture of the roller (although they may be designated by differing terms).

In order to keep main bond area percentage within the limits specified above to preserve softness attributes of the nonwoven web, supplementing or increasing bond area percentage only in the areas of die nonwoven along the cut paths may be an alternative and more desirable solution. FIGS. 5-10 depict schematic z-direction views of portions of webs bearing supplemental edge bond patterns 126. As previously noted, bond impressions 125 may form a main pattern of bonds of the fibers, which imparts and maintains a fabric-like structure to the web. If one or more edge bond patterns 126 are added along cut paths, e.g., cut paths 120, 121, 122, improved cutting and neater, cleaner cut edges can be effected. It is believed that the added edge bond patterns 126 serve to bond in place and/or immobilize (relative the web) a relatively greater number of the fibers forming the web along the cut paths, making the fibers resistive to displacement by the cutting blades and or other displacement or dislodgement as described above without creating cut edges having a scratchy feel that can be uncomfortable to the skin. Prevention of a ragged edge, i.e., a cleaner, neater cut can result. Additionally, with a suitable edge bond pattern 126, fibers that may be freed and/or mobilized in the cutting operation may be more likely to be bonded within the web by the bonds of the edge bond pattern 126, and thus less susceptible to being dislodged in downstream processes and released into the plant environment. As noted, to preserve softness attributes of the larger surface area of the nonwoven, it may be desired to limit this edge bond pattern 126 to only those areas lying along the cut path. Thus, for purposes herein, in this context, "along" is intended to mean confined within 2.0 cm, more preferably 1.5 cm, and still more preferably 1.0 cm of the cut path or cut edge.

Figure 3D:
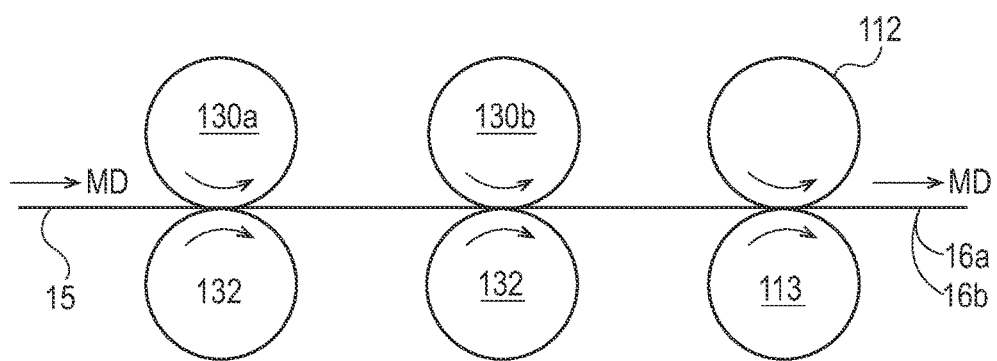
FIG. 3D is a schematic view of a first and second bonding rollers and corresponding anvil rollers, and a cutting blade and an anvil roller, arranged to form sequential bonding and cutting nips and operating on a web, viewed along the cross direction.
Figure 3E:
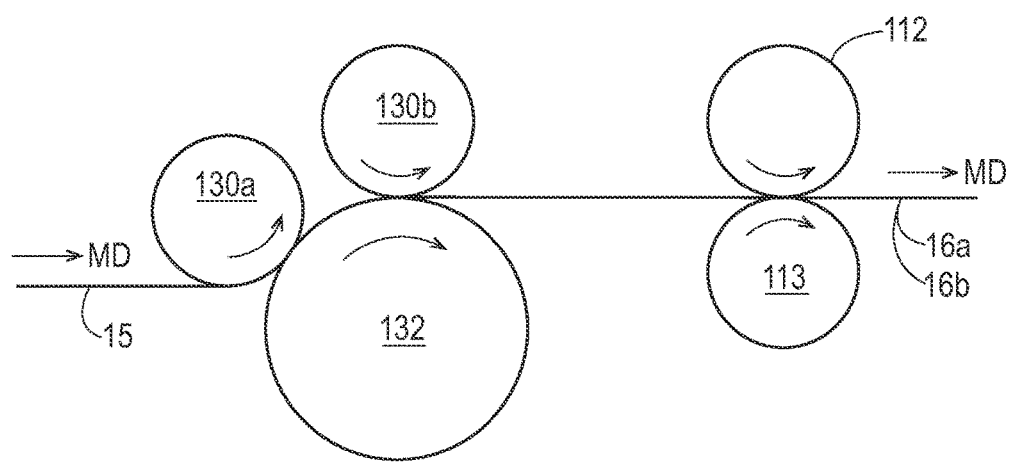
FIG. 3E is a schematic view of a first and second bonding rollers and a common anvil roller, and a cutting blade and an anvil roller, arranged to form sequential bonding and cutting nips and operating on a web, viewed along the cross direction.
Figure 3F:
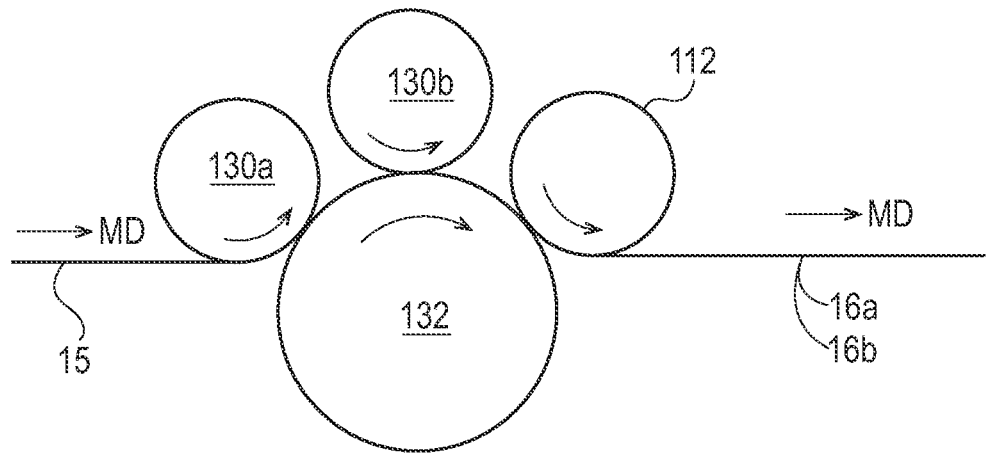
FIG. 3F is a schematic view of a first and second bonding rollers and a cutting blade, and a common anvil roller, arranged to form sequential bonding and cutting nips and operating on a web, viewed along the cross direction.

The edge bond pattern 126 may be imparted to the web by bonding protrusions on first or second pair of bonding rollers situated upstream or downstream of the first bonding roller. In alternative examples, referring to FIGS. 3D-3F, a first bonding roller 130a may bear a main pattern of bonding protrusions designed to impart the main pattern of bonding impressions 125, white a second bonding roller 130b may bear an edge pattern of bonding protrusions designed to impart the edge bond pattern 126, or vice versa. Referring to FIG. 3E, the two bonding rollers 130a, 130b may be disposed about a single anvil/calender roller 132 in planetary fashion, forming two sequential nips, conserving space and helping to ensure precision of relative cross-direction location of the respective main and edge bond patterns. In another alternative, the edge bond pattern 126 may be imparted by additional bonding protrusions corresponding to the desired edge bonding pattern, formed on the same bonding roller 130 as bears the bonding protrusions corresponding to the main pattern. (Herein, the designations "main" and "edge" with respect to bond patterns and calender rollers is not intended to connote an order of placement in the line, an order of processing, or any necessary sequence of processing. The main and edge patterns of bond impressions may be imparted in process(es) that occur simultaneously or sequentially in any order and with or without other processes occurring therebetween.)

In another alternative (not depicted), a cutting nip may be disposed immediately upstream of a bonding nip such that cutting/slitting occurs first but a bonding pattern is impressed along the freshly cut edges immediately thereafter. Again, the cutting and bonding nips may have the same calender/anvil roller in common, in a planetary arrangement of calender/anvil roller, cutting blade, and bonding roller. White this latter arrangement may compromise some of the benefits of applying the bonding pattern along, the cutting path prior to cutting, it also includes some of the benefits, such as bonding fibers along the cut edges so that they are less likely to be dislodged in downstream operations.

Figure 11:
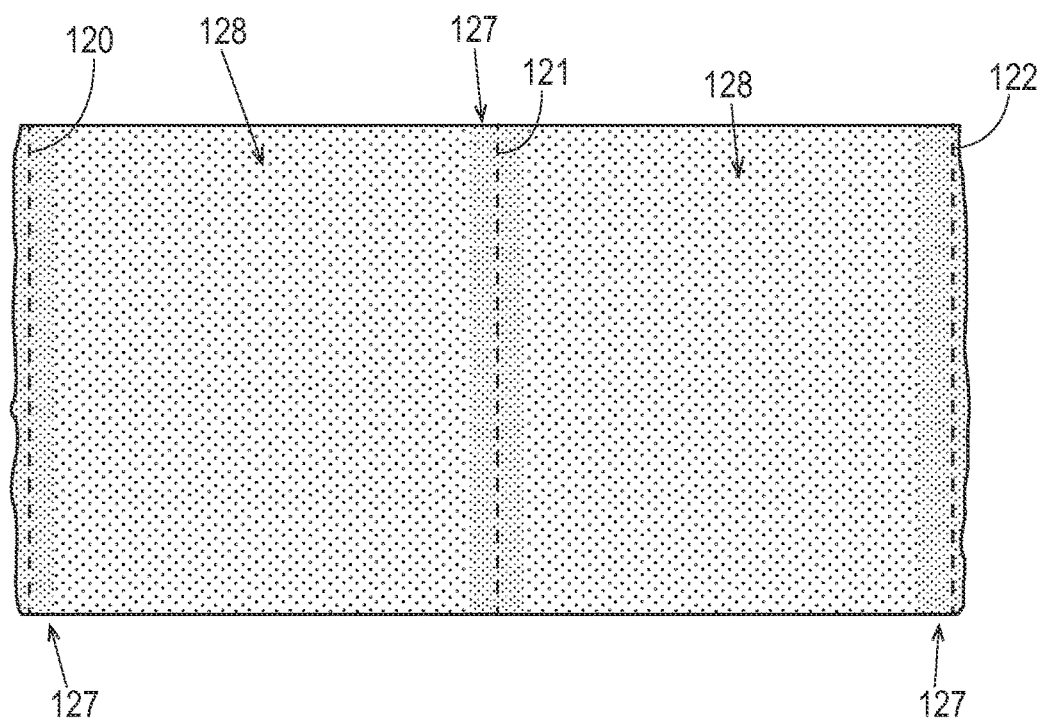
FIG. 11 is a schematic view of is a schematic view of a portion of a nonwoven web, viewed along the z-direction.

The shapes of the bond impressions in the main and edge patterns may be different, or they may be the same. Referring to FIG. 11, the density of the bond impressions (shown as dots in the example of FIG. 11) may vary across the surface of the web, such that density is relatively greater in first locations 127 relatively proximate the cut paths 120, 121, 122, compared with the density of the bond impressions in second locations 128 relatively farther away from the cut paths. The increase in bond density may occur across the nonwoven, as the cut path(s) is(are) approached from locations on the web away from the cut path(s). The increase in bond impression density approaching the cut paths may be abrupt or even step-wise, or may be gradual. Thus, a nonwoven web component of a product such as, e.g., a disposable absorbent article in the form of a diaper, training pant, adult incontinence pant, or feminine hygiene pad may have a bond density that is greater at a location proximate to a cut edge of the nonwoven web than at a location spaced further away from the cut edge. Alternatively, it may be preferable that the one or more calender rollers 130, 130a, 130b bearing the patterns of bonding protrusions, used to calender bond the nonwoven, have combined bonding protrusion density that is greater at locations proximate to a cut path along the nonwoven web component than at locations spaced further away from the cut path. Bonding protrusion density is sometimes specified in engineering drawings and/or specifications for the manufacture of the roller (although they may be designated by differing terms).

Similarly, bond area percentage reflected by the dots in the example of FIG. 11 may vary across the surface of the web, such that bond area percentage is relatively greater in first locations 127 relatively proximate the cut paths 120, 121, 122, compared with the bond area percentage of the bond impressions in second locations 128 relatively farther away from the cut paths. The increase in bond area percentage may occur across the nonwoven, as the cut path(s)

is(are) approached. The increase in bond area percentage approaching the cut paths may be abrupt or even step-wise, or may be gradual. Thus, a nonwoven web component of a product such as, e.g., a disposable absorbent article in the form of a diaper, training pant, adult incontinence pant, or feminine hygiene pad may have a bond area percentage that is greater at a location proximate to a cut edge of the nonwoven web than at a location spaced further away from the cut edge. Alternatively, it may be preferable that the one or more calender rollers 130, 130a, 130b bearing the patterns of bonding protrusions, used to calender bond the nonwoven, have combined bonding protrusion bond area percentage that is greater at locations proximate to a cut path along the nonwoven web component than at locations spaced further away from the cut path. Bond area percentage is sometimes specified in engineering drawings and/or specifications for the manufacture of the roller (although they may be designated by differing terms).

Referring again to FIG. 3C in which a cutting mechanism is illustrated that will cut a curving or laterally varying path along the web material (cutting path varies in location along the cross direction), the edge pattern may also curve or vary laterally, accordingly, to follow the cutting path. The bonding roller(s) used to impress the edge pattern may be configured accordingly.

Bonding along cut paths also may be effected or enhanced by the introduction of a polymer filler to supplement the polymer material of the fibers themselves. A strip or strand of polymer material of similar chemical composition or chemical composition suitably compatible for bonding with the polymer material(s) of the fibers may be introduced upstream of the bonding nip, along the intended edge bonding pattern, so as will be compressed and forced under pressure into the interstices between the fibers in the region of the edge bonding pattern, thereby forming a bonded matrix which captures and bonds the fibers in place along the cut path. In this particular example, the strip or strand also may be in the form of an expressed or extruded bead of melted polymeric material, or hot-melt adhesive, or supplemental strip or sheet of nonwoven or film formed of material having a chemical composition suitably compatible for bonding with the material forming the nonwoven fibers, introduced upstream of the nip.

The edge bonding pattern may be designed with a view toward the nature and general orientation of the fibers of which the web is formed. For example, in a spunbond web, as a result of the manufacturing process, the fibers tend to be relatively longer and generally extend more along the machine direction MD rather than the cross direction, as suggested in FIGS. 4 and 5. Thus, it may be advantageous to design an edge bond pattern 126 in which bond impressions are likely to cross, and thus, bond and capture, fibers proximate to the cut path. For example, see edge bond patterns 126 in FIGS. 5-8. It may be particularly advantageous that the edge pattern comprises a row of bond impressions in the shape of bars forming angles between 10 degrees and 90 degrees with the machine direction, more preferably between 20 degrees and 80 degrees, and still more preferably between 30 degrees and 70 degrees. It also may be advantageous that the edge pattern comprise a pattern of bond impressions in the shape of crossing bars, as suggested in FIG. 8.

For nonwoven webs having a basis weight of 6 gsm to 50 gsm, it may be desirable that the bond area percentage of the edge pattern (distinct from the bond area percentage of the main pattern) be from 20 to 100 percent, and more preferably from 40 to 80 percent. Alternatively, it my be preferable that the calender roller 130 bearing the pattern of bonding protrusions, used to impart the edge bonding pattern, have a bonding area percentage of from 20 to 100 percent, and more preferably from 40 to 80 percent, along the portion which rolls over the nonwoven to impart the edge bond pattern during the process. Bonding area percentage is sometimes specified in engineering drawings and/or specifications for the manufacture of the roller (although they may be designated by differing terms).

When a nonwoven is of a relatively lower basis weight (in the range of 3 gsm to 25 gsm), the design and extent of surface area occupied by the edge pattern of bonds may require a differing approach. As basis weight decreases, fiber density per unit web surface area decreases. The individual bonding protrusions on the bonding roller generally encounter fewer fibers in the bonding process. In this circumstance, particularly in thermal bonding, bonding "burn-through" can become a problem. When a system is susceptible to burn-through, a reduced number of fibers means a reduced amount of polymeric material that is available to be melted and bonded beneath a bonding protrusion, to create a bond site of compressed and fused material. In some circumstances the relatively small amount of polymeric material present in fibers beneath a bonding protrusion will simply melt and be expressed substantially or entirely from between the bonding protrusion and opposing roller surface as the material passes through the nip. A hole through the web at the intended bond site results. Such holes can be unsightly and, if present along a cut path, can result in a cut edge having a ragged appearance. In wearable articles, such an edge can feel scratchy and uncomfortable to the skin.

Two approaches may be employed to utilize an edge pattern of bonds to provide a neat and clean cut edge, white addressing the problem of burn-through. In a first approach, the edge pattern is simply a continuous band or strip of bonding extending along the cut path, rather than a pattern of discrete shapes. In other words, the edge bond pattern has a bond area percentage of 100 percent; nearly all or all fibers within the band or strip have been compressed, deformed and/or fused together and no discrete bond impressions are discernible. In a second approach, the edge bond pattern may still comprise a pattern of bond impressions having discrete shapes, such as circles, ovals, diamonds, squares, rectangles, triangles, etc., having an aspect ratio of less than 20:1, more preferably less then 10:1, and even more preferably less than 2:1. The bond impressions may have an average size of from 0.05 to 0.15 mm$^2$, more preferably, 0.08 to 0.12 mm$^2$. This relatively small size helps ensure that any burn-through holes that occur are sufficiently small as to be largely unnoticeable to the naked eye. Similarly, the bonds successfully formed of such small shapes are not highly noticeable and may be desired for appearance reasons. In connection with these relatively small-size bond shapes, to ensure sufficient bonding, it may be desirable that the impressions have a density such that bond area percent is from 20 to 100 percent, and more preferably from 40 to 80 percent. Alternatively, it may be preferable that the calender roller 130 bearing the edge pattern of bonding protrusions have bonding a area percentage of from 20 to 100 percent, and more preferably from 40 to 80 percent. As noted, bonding area percentage and/or bonding protrusion density are sometimes specified in engineering drawings and/or specifications for the manufacture of the roller (although they may be designated by differing terms). Either approach may help ensure that most of the fibers proximate to the cut path are captured by the bonds.

From the foregoing it may also be appreciated that the bonding and slitting processes described above may include more than one layer of nonwoven web. For example, two or more layers of nonwoven web may be bonded together along a cut path along which both layers will be cut, at the greater bond/bonding area percentages described above, prior to cutting along the cut paths. This process may be useful, e.g., to firm an envelope-like structure for containing components between the two layers of nonwoven web. It may provide the advantages described herein, including neater, cleaner cut edges and reduced release of nonwoven fibers into the plant environment.

In addition to providing neater, cleaner cut nonwoven web edges and reducing the incidence of release of loose fibers into the plant environment, the approaches described above may provide further advantages. The added bonds along the cut edges may serve to improve mechanical properties, e.g., tensile strength, of the nonwoven web. This is beneficial for downstream processes which require a sufficient level of web strength and/or dimensional stability, and is also useful when the nonwoven web will be used as a component in an application in which it is needed to impart strength to the product (such as when used as a component of a diaper backsheet). An edge pattern of bonds along cut paths also may help reduce variations in forces borne by the cutting mechanism, extend time between needed cutting blade sharpening (reducing line down time), and increase cutting blade life. A cut edge of a nonwoven having a pattern of bonding therealong may also have the appearance of a neatly hemmed edge.

Bond Area Measurement Method

Area measurements are performed on images generated using a flat bed scanner capable of scanning at a resolution of at least 4800 dpi in reflectance mode (a suitable scanner is the Epson Perfection V750 Pro, Epson, USA). Measurements are performed using ImageJ software (Version 1.43u, National Institutes of Health, USA) and calibrated against a ruler certified by NIST.

Samples of the subject nonwoven web that are 80 mm by 80 mm are used. Precondition the samples at about 23° C.±2 C.° and about 50%±2% relative humidity for 2 hours prior to testing. Identify the machine direction of the nonwoven web and draw a fine line on each sample along the machine direction to enable scanned images to be aligned.

Place the sample to be measured on the flat bed scanner, with the surface bearing the bond impressions or bond shapes facing downward, with the ruler directly adjacent. Placement is such that the dimension corresponding to the machine direction of the nonwoven is parallel to the ruler. A black backing is placed over the specimen and the lid to the scanner is closed. Acquire an image composed of the non-woven and ruler at 4800 dpi in reflectance mode in 8 bit grayscale and save the file. Open the image file in ImageJ and perform a linear calibration using the imaged ruler.

Unless otherwise stated, dimensional and area measurements are made in triplicate, of three similar bond shapes on each sample for 6 similar samples. The 18 values are averaged and reported.

Bond Area Percentage

Identify a single repeat pattern of bond shapes and areas between them and enlarge the image such that the repeat pattern fills the field of view. In ImageJ, draw a rectangle that circumscribes the repeat pattern. Calculate area of the rectangle and record to the nearest 0.001 mm$^2$. Next, with the area tool, trace the individual bond shapes or portions thereof that are entirely within the repeat pattern/rectangle and calculate and add the areas of all bond shapes or portions thereof that are within the repeat pattern/rectangle. Record to the nearest 0.001 mm$^2$. Calculate as follows:

$$\text{Bond Area \%} = (\text{Sum of areas of bond shapes within repeat pattern})/(\text{total area of repeat pattern}) \times 100\%$$

Repeat for a total of three non-adjacent regions randomly selected across the sample. Record as Percent Bond Area to the nearest 0.01%. Calculate the average and standard deviation of all 18 of the bond area percentage measurements and report to the nearest 0.01%.

Average Individual Bond Area

Enlarge the image of a region of the sample such that edges of a bond shape can be identified. With the area tool, manually trace the perimeter of a bond. Calculate and record the area to the nearest 0.001 mm$^2$. Repeat for a total of five non-adjacent bonds randomly selected across the total sample. Measurements are made on each sample. A total of six samples are measured. Calculate the average and standard deviation of all 30 bond area measurements and report to the nearest 0.001 mm$^2$.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A process for producing a nonwoven web material having a cut edge, comprising the steps of:
   forming a batt of polymeric fibers;
   consolidating the batt in a z-direction and thereby forming a nonwoven web material;
   conveying the batt or the nonwoven web material along a machine direction to one or more nips between one or more pairs of bonding rollers and anvil rollers rotating about axes lying substantially along a cross direction;
   impressing a first pattern of bond impressions into the batt or the nonwoven web material in a first nip, the pattern of bond impressions lying along a cut path, and thereby bonding the batt or the nonwoven web material along the cut path, the first pattern of bond impressions having a first bond area percentage and a density, wherein:
      the density varies in a cross direction across a surface of the nonwoven web, wherein the density is relatively higher at a first location relatively proximate the cut path, and relatively lower at second location farther away from the cut path; and the first bond area percentage varies in the cross direction across the surface of the nonwoven web, wherein the first bond area percentage is relatively higher at the first location relatively proximate to the cut path, and relatively lower at the second location farther away from the cut path;

cutting the nonwoven web material along the cut path and within the first pattern of bond impressions;

impressing a second pattern of bond impressions into the batt or the nonwoven web material in a second nip, the second pattern of bond impressions being distinct from the first pattern of bond impressions and having a second bond area percentage, and bonding the batt to form a bonded nonwoven web material;

wherein the second bond area percentage is between 3 and 45 percent; and wherein at least a portion of the fibers are multicomponent fibers.

2. The process of claim 1 wherein heating energy is applied to the batt or nonwoven web material at at least one of the one or more nips, thereby creating thermal bonds in the nonwoven web material.

3. The process of claim 1 wherein the first pattern of bond impressions is discrete and does not continue across the entirety of the nonwoven web material in a cross direction thereof, and the first bond area percentage is greater than the second bond area percentage.

4. The process of claim 3 wherein the first bond area percentage is between 20 and 80 percent.

5. The process of claim 1 wherein the first pattern of bond impressions extends to the cut path, and comprises bond impressions in the shape of discrete bars that are continuous to the cut path.

6. The process of claim 5 wherein the discrete bar shapes extend along lines that form angles with a machine direction axis along the web, the angles being between 10 degrees and 90 degrees.

7. The process of claim 6 wherein said lines comprise at least two sets of lines that cross such that the bar shapes form a pattern of crossing bar shapes.

\* \* \* \* \*